United States Patent [19]

Wagner et al.

[11] Patent Number: 5,410,037
[45] Date of Patent: Apr. 25, 1995

[54] PROCESS FOR SILYLIZING CARBOHYDRATES, AND USE OF THE SILYLIZED CARBOHYDRATES

[75] Inventors: Thomas Wagner, Wenden; Werner Mormann, Kreuztal, both of Germany

[73] Assignee: Rhone-Poulenc Rhodia Aktiengesellschaft, Freiburg, Germany

[21] Appl. No.: 210,877

[22] Filed: Mar. 18, 1994

[30] Foreign Application Priority Data

Mar. 23, 1993 [DE] Germany ............... 43 09 297.7

[51] Int. Cl.⁶ .................. C08B 15/05; C08B 31/00; C07H 23/00
[52] U.S. Cl. ..................... 536/121; 536/84; 536/101; 536/120; 536/121
[58] Field of Search ............ 536/18, 6, 56, 84, 101, 536/102, 111, 120, 121, 124

[56] References Cited

U.S. PATENT DOCUMENTS

| | | | |
|---|---|---|---|
| 3,418,312 | 12/1968 | Klebe | 536/56 |
| 3,418,313 | 12/1968 | Klebe | 536/56 |
| 3,432,488 | 3/1969 | Finkbeiner et al. | 536/56 |
| 4,390,692 | 6/1983 | Green | 536/56 |
| 4,474,950 | 10/1984 | Felcht et al. | 536/43 |

FOREIGN PATENT DOCUMENTS

| | | |
|---|---|---|
| 0562378 | 9/1993 | European Pat. Off. |
| 3104531 | 3/1981 | Germany. |
| 263416 | 1/1989 | Germany. |

OTHER PUBLICATIONS

Das Papier, G. Greber et al "Silylderivate der Cellulose", pp. 551-553-vol. 35, No. 12, 1981, Darmstadt-pp. 547-554.
Journal Of Applied Polymer Science, vol. 26, 1981, pp. 3827-3836 Geoffrey K. Cooper et al. Trimethylsilyl Cellulose as Precursor to Regenerated Cellulose Fiber.
R. E. Harmon, K. K. De, S. K. Gupta, "New Procedure for Preparing Tri-Methylsilyl Derivatives of Polysaccharides"; Carbohydrate Research, 31 (1973) 407-409.
R. E. Harmon, K. K. De. S. K. Gupta, "Preparation of Trimethylsilyl Derivatives of Polysaccharides"; Die Starke 25, 1973, 429-431.
J. F. Klebe, H. L. Finkbeiner, "Silyl Celluloses; A New Class of Soluble Cellulose Derivatives"; J. Polym. Sci. Part A-1, 7 (1969), 1947-1958.

Primary Examiner—Nathan M. Nutter
Attorney, Agent, or Firm—Bucknam and Archer

[57] ABSTRACT

There is described a process for silylizing carbohydrates in liquid nitrogen compounds,
the carbohydrates being reacted under pressure in an autoclave at a tempperature of about 0° to 200° C. with a silylizing agent of the formula (I)

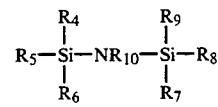

in a liquid nitrogen compound of the formula (II)

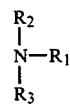

the respective radicals in the two formulas (I) and (II) being, independently of each other:
hydrogen, a low alkyl group with 1 to 4 carbon atoms, a cycloalkyl group with 3 to 6 carbon atoms, an aryl group in the form of a phenyl or naphthyl radical, an aralkyl group with 7 to 18 carbon atoms, an alkylaryl group with 7 to 18 carbon atoms, or an O-, S- or N-containing heterocyclic group with 2 to 5 carbon atoms.

An especially suitable silylizing agent is hexamethyl disilazane. As liquid nitrogen compound preferably ammonia is taken, which under the process conditions is liquid. The process according to the invention is of advantage ecologically and economically. The products obtained according to the invention are especially pure, making further processing possible.

14 Claims, No Drawings

PROCESS FOR SILYLIZING CARBOHYDRATES, AND USE OF THE SILYLIZED CARBOHYDRATES

The invention relates to a process for silylizing carbohydrates in liquid nitrogen compounds and to various applications of use of the silylized carbohydrates obtained thereby.

By silylizing carbohydrates, their chemical and physical properties can be changed drastically. The silylizing is done by binding trialkylsilyl groups to the hydroxyl groups of the carbon atoms 2, 3 and 6 of the anhydroglucose unit with formation of Si—O bonds. Trimethylsilyl derivatives of carbohydrates having an average degree of substitution of about 2.5 are known (cf. among others H. A. Schuyten et al. in J. Am. Chem. Soc. 70, 1919 ff (1948)). The most common silylizing agent is the readily accessible chlorotrimethyl silane. Thus, according to numerous papers, cellulose has been reacted with chlorotrimethyl silane in pyridine as reaction medium to trimethylsilyl cellulose. The pyridine served at the same time as swelling agent and as acid acceptor of the heterogenic reaction.

In J. Am. Chem. Soc. 70, 1919 ff (1948) the preparation of a silyl derivative of cellulose is described for the first time. Trimethylsilyl derivatives with at most 2.75 trimethylsilyl groups per anhydroglucose unit of the cellulose were obtained under heterogenous conditions by reacting cellulose as cotton linters and cellulose acetate with chlorotrimethyl silane in pyridine under reflux. This trimethylsilyl cellulose was stable in air at room temperature. It decomposed at higher temperatures or in the presence of moisture. It was hydrolyzed very quickly in boiling water or in dilute acids and bases. With partially acetylized cellulose only the free hydroxyl groups reacted, resulting in a total degree of substitution of almost 3.

According to J. Polym. Sci. Part A-17, 1947 ff (1969), trimethylsilyl cellulose again with 2.7 trimethylsilyl groups per anhydroglucose unit is obtained by a 7-hour reaction at 160°-170° C. of cellulose with bis (trimethylsilyl)-acetamide as silylizing reagent in N-methyl pyrrolidone and xylene as solvent. By a 10-hour treatment of this trimethylsilyl cellulose with boiling water only 50% of the trimethylsilyl groups were hydrolyzed. This surprisingly high resistance to hydrolysis is attributed to steric factors. Besides trimethyl cellulose, other triorganosilyl celluloses have been produced, which were of interest primarily as electric insulating material because of their low relative dielectric constant.

In Ind. Eng. Chem. 45, 2542 ff (1953) the silylization of starch is described for the first time. Here corn starch is reacted with chlorotrimethyl silane as silylizing reagent to formamide and a product having a degree of substitution up to 2.0 is obtained.

In Makromol. Chem. 21, 59 ff (1956) transferring the silylization from glucose to pectin is described. With various alkyl and aryl chlorosilanes derivatives of a degree of substitution under 1 were obtained.

In Makromol. Chem. 126, 139 ff (1969) the synthesis of 2,3,6-tris-0-trimethylsilyl amylose and cellulose by reaction of the carbohydrates in the melt (170° C.) with N-trimethylsilyl acetamide is described. In contrast to trimethylcellulose regenerated from acetyl cellulose, the silylization of native cellulose linters gave degrees of substitution of only 2.4.

According to Makromol. Chem. 120, 87 ff (1968), persilylization of amylose and cellulose is possible by heterogenous reaction of the respective carbohydrates for 3 hours at 15° C. in pyridine with chloromethyl silane. For native cellulose, that is cotton linters the reaction had to be repeated, free hydroxyl groups were still present, in contrast to cellulose reprecipitated from cuoxam (Schweizer's reagent). A complete substitution of the branched polysaccharides dextran and amylopectin was not achieved.

Since in the case of silylizing with chlorotrimethyl silane in the presence of tertiary amines or ammonia, the hydrochloride is always obtained as a by-product or impurity, Harmon et al (cf. Carbohyd. Res. 31, 407 ff (1973) and "Die Sta rke" 25, 429 ff (1973)) used hexamethyl disilazane as silylizing agent. Thus they prepared in pyridine or in formamide, a highly polar organic solvent, at 70° C. trimethylsilyl derivatives of starch, amylose, amylopectin, glycogen, chitin, dextrins, pectin and cellulose. The trimethylsilyl derivative of polysaccharides is here precipitated for example because the solution in formamide is poured into anhydrous acetone. Only cellulose and low-molecular dextrins were completely silylized. Even the likewise unbranched amylose was silylized only to a degree of substitution of 2.2. By comparison, the trimethylsilyl derivative of the branched polysaccharide amylopectin contained only 0.9 trimethylsilyl groups per anhydroglucose unit.

The object of all of the above described work on silylization of carbohydrates was primarily to obtain trimethylsilyl derivatives of a high degree of substitution which are soluble in organic solvents and can be used as hydrophobic films, papers and diaphragms.

To avoid the limited influences that result from the high molecular weight of the carbohydrates and a consequent multiphase reaction process, there was used for cellulose also a number of non-aqueous solvents. Thus, cellulose was modified by treatment with derivatizing systems, such as dinitrotetroxide/N,N-dimethyl formamide (cf. R. G. Schweiger, Tappi 57, 86 ff (1974)) or dimethyl sulfoxide/paraformaldehyde (cf. N. Shirashi et al., Sen'i Gakkaishi 35, 466 ff (1979)), with formation of soluble unstable derivatives (nitrites or hydroxymethyl ethers) and functional groups formed by subsequent secondary reactions at the hydroxyl groups or at the intermediately formed functional groups, which were split off again. Here, trimethylsilyl derivatives of cellulose with N,O-bis (trimethylsilyl)-trifluoroacetamide were prepared in the solvent system dimethylsulfoxide/paraformaldehyde. Degrees of substitution of only 2.4 were attained despite a homogenous reaction process (cf. Shirashi et al, Sen'i Gakkaishe 35, 466 (1979)).

Another possibility for homogenous modification of cellulose is dissolution in specific non-derivativizing solvent systems, such as N,N-dimethyl-acetamide/lithium chloride (cf. W. Schempp et al., Das Papier 38, 607 ff (1984) or N-methyl-morpholin-N-oxide (cf. I. F. Kennedy et al., Cellulose, Ellis Horwood Ltd., Chichester 1990), with subsequent reaction at the hydroxyl groups "Des Papier" 38 607 ff (1984) describes for the first time the synthesis of highly substituted trimethylsilyl celluloses in the system N,N-dimethylacetamide/lithium chloride and hexamethyldisilazane as silylizing agent for the purpose of as complete as possible substitution for determining the molar mass distribution by means of gel permeation chromatography.

In J. Polym. Sci., Part B: Polym. Phys. 26, 1101 ff (1988) the study of liquid-crystal properties of trialkyl cellulose is described.

According to "Das Papier" 38 607 ff (1984), only stoichiometric quantities of hexamethyl disilazane are required even for degrees of substitution of almost 3. For higher molecular weight cotton linters and spruce pulps again only degrees of substitution of 2.7 occurred.

In various literature sources (inter alia Z. Chem. 24, 62 ff (1984), Z. Chem. 27, 1 ff (1987), Makromol. Chem., Rapid Commu. 9, 569 ff (1988), Makromol. Chem. 191, 2985 ff (1990) and Das Papier 44, 624 ff (1990)) are described the utilization and accessability of trimethyl silyl celluloses as soluble and stable intermediate products for regioselective homogenous derivatizations of cellulose. A thus controlled introduction of active groups makes it possible, for example, to produce cellulose materials of a defined degree of substitution and controlled substituent distribution as adsorbents for chromatography, support materials for active substances, bioactive polymers, liquid-crystal macromolecules, photoactive layers and a variety of diaphragms. Here, the potential of innovation, far from being exhausted, in the field of preparative cellulose chemistry manifests itself. This is of increasing interest in view of the object to create new materials and active substances on the basis of after-growing polysaccharide raw materials.

In the early 'eighties, trimethylsilyl celluloses were taken into consideration, because of their good solubility and the easy hydrolysis of the silyl ether substituents, as potential material for regenerated cellulose processes (cf. Das Papier 35, 547 ff (1981) and J. Appl. Polym. Sci 25, 3827 ff (1981)), but industrial use did not occur. Thus, cellulose was silyzed with hexamethyl disilazane with addition of small amounts of chlorotrimethylsilane/pyridine in DMF, and a thermoplastic material was obtained which could be spun to a fiber from the melt at 320° C. Acid hydrolysis of these fibers with dilute aqueous acids gave cellulose having properties comparable to those of commercially available rayon fibers (cf. J. Appl Polym. Sci 26, 3827 ff (1981)). As pyridine and DMF are questionable as reaction media both ecologically and economically and besides are difficult to remove from polymeric materials, the attempt has been made to avoid the xanthogenate process via the soluble trimethylsilyl cellulose with ammonia as reaction medium. Thus, cellulose was reacted with chlorotrimethylsilane in liquid ammonia which served as swelling agent and also as reaction medium and hydrochloric acid acceptor. The pulp was swelled at atmospheric pressure in liquid ammonia at 70° C. and mixed with the quantity of chlorotrimethyl silane referred to a trisubstitution. Due to the enormous affinity of silicon to oxygen, the silylization occurred in the stated manner, i.e. the chlorotrimethyl silane reacted directly with the hydroxyl groups of the cellulose. After completion of the reaction, the excess ammonia was recovered, and the trimethylsilyl cellulose, soluble in several organic solvents, was dissolved out of the residue (Greber et al., Das Papier 35, 547 ff (1981)).

The special advantage of this trimethylsilyl cellulose process is that it permits a cycle in which recovery or regeneration of almost all reagents involved is possible. In terms of process technology, however, even such a functioning cycle would not be acceptable because, while the objectionable reaction medium pyridine is avoided, it still operates with the halogen-containing and corrosive silylizing agent chlorotrimethyl silane. Besides, this type of silylization always produces insoluble ammonium chloride as a by-product or impurity, making it difficult to isolate and purify the trimethylsilyl cellulose.

DE-OS 3104531 covers a process for the production of a new O-trimethylsilyl cellulose of a degree of substitution up to 2.0, preferably 1.4 to 1.6, where wood or cotton celluloses are swelled in dry, liquid ammonia and then reacted with trimethyl chlorosilane, the reaction product being dissolved in a highly polar aprotic solvent and possibly processed to a purified dry product by precipitation. Suitable as strongly polar solvents are said to be in particular dimethyl formamide (DMF), dimethyl acetamide (DMA), N-methylpyrrolidone (NMP) and dimethyl sulfoxide (DMSO). Except for Example 3, trimethyl chlorosilane is always aimed at as silylizing agent, although one form of realization of the known process is said to consist of "adding preformed hexamethyl disilazane to the cellulose swelled with ammonia". One operates in liquid ammonia under normal pressure, which after completed reaction can be removed by heating and evacuating or by neutralizing. Purification is said to be effected by dissolving in highly polar solvents, such as dimethyl acetamide and dimethyl formamide, and separating the insoluble ammonium chloride.

The inventors named in DE-OS 310453 1 recanted the statements concerning Example 3 in a subsequently written article in Das Papier 35, p. 551, right column, 1981, saying literally: "The second possibility, that the silylization reaction occurs with the aid of hexamethyl disilazane—which forms from trimethyl chlorosilane and ammonia (cf. FIG. 10—, we were able to exclude because under various reaction conditions the silylization of cellulose in liquid ammonia with preformed hexamethyl disilazane did not succeed" (loc. cit. p. 551, right column, para. 2). Thereby they emphatically denied the suitability of hexamethyl disilazane for the silylization of carbohydrates in liquid ammonia at normal pressure. Hence they leave no doubt that the technical teaching given in Example 3 of DE-OS 3104531 is not feasible.

U.S. Pat. No. 4,390,692 describes the production of trimethylsilyl cellulose esters with the use of hexamethyl disilazane. It makes reference to the fact that most of the known methods require a large amount of solvents for dispersing the cellulose, and thereafter the solvents must be separated from the silylized cellulose product. The solvent quantity should therefore be reduced and a high degree of silylization should be aimed at, which however actually seems to be at most 2.19. To solve the problems addressed, the silylization with hexamethyl disilazane is carried out in the presence of a small amount of a catalyst. As "catalysts" are used, among others, acetamide and N, N-dimethyl formamide, highly polar aprotic solvents. It is said to be advantageous to use, in addition to these highly polar solvents, an ammonium halide (known to be corrosive), for example ammonium chloride. The teaching according to U.S. Pat. No. 4,390,692 uses. Therefore, highly polar solvents in a relatively small quantity, evidently to form at least one wetting phase for the silylization reaction. That we are here not dealing with "catalytic" quantities in the usual sense is evident directly from the weight ratio of hexamethyl disilazane to e.g. N,N-dimethyl formamide of about 10:1 to 20:1, given in U.S. Pat. No. 4,390,692. To improve the dissolution, not the "catalyzing" function of the highly polar solvents, the reaction temperatures are to be set at about 100° to 135° C.

Also the literature reference "Journal of Polymer Science" Part A 1, Vol. 7, (1969), 1947–1958 expressly mentions, when hexamethyl disilazane is used as silylizing agent of carbohydrates, the operating in a strongly polar solvent of high boiling point. These solvents are difficult to remove and normally toxic.

It is the object of the invention to provide a process for silylizing carbohydrates in liquid nitrogen compounds which offers advantages both economically and ecologically, allows a product of a high degree of substitution or silylization and improved purity to be produced which can advantageously be melt-spun, the fibers obtained thereby as well as the desilylized fibers obtainable therefrom having improved ultimate tensile strength values over comparative products. In particular it is possible to avoid the use of highly polar solvents difficult to remove.

According to the invention, this problem is solved in that the carbohydrates are reacted under pressure in an autoclave at a temperature of about 0° to 200° C. with a silylizing agent of the formula (I)

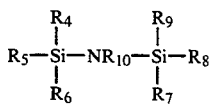

in a liquid nitrogen compound of the formula (II)

the respective radicals in the two formulas (I) and (II) being, independently of each other:
hydrogen, a low alkyl group with 1 to 4 carbon atoms, a cycloalkyl group with 3 to 6 carbon atoms, an aryl group in the form of a phenyl or naphthyl radical, an aralkyl group with 7 to 18 carbon atoms, an alkylaryl group with 7 to 18 carbon atoms, or an O-, S- or N-containing heterocyclic group with 2 to 5 carbon atoms.

Preferably the reaction between the two compounds of formula (I) and (II) is carried out in a temperature range from about 25° to 150° C. and in particular between about 50° and 120° C. It is important that the reaction takes place in an autoclave or vessel for heating under pressure, so that at elevated temperature at least a sufficient part of the nitrogen compound of formula (II) is present in the liquid state. The quantity of liquid phase of this nitrogen compound should suffice to wet the carbohydrate to be silylized at least to the extent that the desired reaction will occur in the wetting phase. Appropriately there are per 10 parts by weight of carbohydrate to be silylized, in particular in the form of cellulose, at least about 1 part by weight of ammonia compound, preferably at least about 3 parts by weight and in particular about 5 parts by weight of liquid nitrogen compound, in particular in the form of ammonia. For economic reasons this quantity ratio should be optimized, as an excess of liquid nitrogen compound offers no advantages. Preferably the reaction occurs in a continuous phase of the liquid nitrogen compound, as the liquid nitrogen compound serves not only as reaction medium for the non-soluble carbohydrates but also as swelling agent. Moreover, it intervenes also in the reaction processes, as it is a proton acceptor and hence, as must be assumed, supports at least the detachment of the proton of the hydroxyl group of the carbohydrate, so that the oxygen of this group then optimizes the desired silylization due to its strong affinity to the silicon atom.

To achieve an optimization of the process according to the invention, it is preferred to match the silylizing agent and the liquid nitrogen compound that are chosen in each case. Preferably two of the radicals $R_1$, $R_2$ and $R_3$ are hydrogen, and one radical is identical with the radical $R_{10}$, to be explained later, of the silylizing agent of formula (I). This brings it about that on completion of the silylizing process the group "$NR_{10}$" is converted to substituted ammonia of the formula $NH_2R_{10}$, and $R_{10}$ then equals for example $R_1$ of formula (II) with $R_2$ and $R_3$ being hydrogen. Upon completion of the silylizing reaction, a uniform liquid nitrogen compound is then discharged from the opened autoclave. It is especially advantageous to use as liquid nitrogen compound of formula (II) the ammonia that is liquid under the process conditions, so that $R_{10}$ in formula (II) of the silylizing agent is then likewise hydrogen.

In the above formulas (I) and (II) the respective radicals are preferably hydrogen, as the corresponding starting compounds are commercial or easier [sic] to produce. However, also the further possibilities as given in the above definition of the invention are sitable under the invention. Possible low alkyl groups with 1 to 4 carbon atoms are the methyl, ethyl, n-propyl, i-propyl groups as well as the various isomers of the butyl group. The cyclo-alkyl group with 3 to 6 carbon atoms includes under the invention in particular the cyclopropyl, cylcobutyl and cyclopentyl radical, the aralkyl group with 7 to 18 carbon atoms includes in particular the benzyl and phenethyl group, the alkylaryl group with 7 to 18 carbon atoms includes in particular the tolyl group, and the heterocylcic group with 2 to 5 carbon atoms includes in particular those in whose heterocyclic ring at least one oxygen, sulfur or N atom is present, where the radicals of oxirane, tetrahydrofurane, di-oxane and pyrane may be cited as suitable examples. Determining for the above-mentioned substituents is that they ensure the chemical mechanisms taking place under the process according to the invention or do not interfere with it. In the spirit of the invention, therefore they should facilitate the silylization of the carbohydrates and should moreover permit possible further processing of the silylized carbohydrates, for example desilylization or reaction with further reagents. The above definitions of the various radicals $R_1$ to $R_{10}$ should comprise also the possibility that likewise non-interfering substituents are introduced, for example again a low alkyl group with 1 to 4 carbon atoms or suitable halogen atoms, such as chlorine.

Preferably the nitrogen compound of formula (II), liquid under the process conditions, is ammonia or a primary, secondary or tertiary amine, as in particular methyl or ethyl amine, dimethyl or diethyl amine, and trimethyl or triethyl amine.

The above statements about the substituents $R_1$ to $R_3$ with regard to the substituents entering into consideration apply analogously to the radicals $R_4$ to $R_{10}$ of Formula (II) of the silylizing agent. An especially suitable silylizing agent is hexamethyl disilazane, which leads to excellent sylilizations and is preferably charged into liquid ammonia.

It is surprising that, despite the clear statements in "Das Papier", 35, p. 551 right col. (1981), the sylylization of carbohydrates with hexamethyl disilazane in ammonia is successful in a most advantageous manner, this being possible without the use of highly polar solvents, and that a product having a degree of silylization up to 3 is obtainable. This literature reference does not contain details about the unsuccessfully performed processes.

The quantitative ratio of silylizing agent to the chosen carbohydrate is not critical for the conduction of the process of the invention. The quantity ratio depends on the hoped-for or highest possible degree of substituation. The man of the art is readily able to determine by simple experiments the optimum ratio of silyl groups of the silylizing agent used to the OH groups of the monomer units of the particular carbohydrate, for example anhydroglucose units in starch or cellulose. In the specific case also the cellulose or starch starting material plays a role. Thus, for the silylizing agents used according to the invention, in particular in the form of hexamethyl disilazane, one could take the ratio of silyl groups from silylizing agent used per OH group of the anhydroglucose units of the respective polysaccharide, in particular cellulose, at preferably about 5:1 to 1:1, in particular 3:1 to 1:1, in order, as the following Table I shows, to obtain a degree of substitution of at least 1.9 or 2.1 and in particular 2.5 or more. Increasing the quantity of silylizing agent, in particular hexamethyl disilazane, over the mentioned ratio of abut 5:1 does not lead to any increase of the degree of substitution. For optimum process conduction the quantity of the particular silylizing agent should be chosen so that it is consumed as completely as possible, so that after the reaction medium is discharged, in particular in the form of ammonia, only the reaction product remains in the autoclave.

In specific cases it may be of advantage, in carrying out the process of the invention, to have present in the reaction medium not only the silylizing agent, the carbohydrate to be silylized, and the nitrogen compound liquid under the reaction conditions, but to add into the reaction medium inert solvents as well, such as hexane, toluene and THF (tetrahydrofunane). These are inert solvents that are liquid at room temperature of about 20° C. Afteer evaporation of the liquid nitrogen compound, in particular in the form of ammonia, these inert solvents remain and convert the silyzized carbohydrates into a solution that can be processed further. For example, a polar solvent such as methanol or ethanol may be added to these solutions so that the silylized product is precipitated in that manner. Thus it can be spun wet or dry in a suitable solution. While this is true also for the above discussed products obtained by known processes, they are not equally pure.

The above statements show that the process products obtained are insoluble in polar solvents but soluble in nonpolar solvents. This is a special characteristic of the silyzized carbohydrates obtained according to the invention, in particular in the form of silyzized cellulose. In the spirit of the invention, "nonpolar solvents" means in particular those having a dielectric constant of at most about 3, reference being made with respect to the determination of the dielectric constant to Römpp Chemie Lexikon, 9th ed., vol. 2, 1990, p. 955 right column to p. 956, left column. This includes for example benzene and carbon tetrachloride, whose dielectric constant is 2.3 and 2.2 respectively. By contrast, the solvents methanol, nitrobenzene and formamide, to be rated as polar or even highly polar, have dielectric constants of 33.5, 35.7 and 109.

The pure product obtained according to the invention can be subjected to any desired further reactions. Thus the residual free hydroxyl groups can, for example, be reacted with acylizing agents, for which in particular acetylizing agents enter into consideration. Suitable acetylizing agents include in particular acetic acid anhydride and acetyl chloride, the acetylation taking place in the usual manner and preferably in the presence of a solvent, such as benzene, acetic acid and the like, possibly also in the presence of catalysts. The acetylation is not a subject of the present invention. It is to be shown merely that the pure products obtainable according to the invention are especially suitable for this purpose.

The process of the invention is not critically limited with respect to the type of carbohydrates to be silyzized. In principle, mono-, di- and polysaccharides can be silyzized by it. The process of the invention is especially suitable for the silylization of sucrose, starch and cellulose, and of products derived therefrom which are degraded more or less, for example dextrins.

As to the type of autoclave to be used for carrying out the process of the invention there are no special requirements. The term "autoclave" should be understood in the spirit of thee invention in the widest possible sense. The determining factor is that during the reaction the required pressure is set in the selected reaction apparatus, to be able to maintain the process parameters important for the process of the invention. Hence one could understand by an autoclave in the sense of the invention also a suitably designed extruder, where for example ammonia under pressure is liquefied and the proper temperatures prevail. This makes possible also an advantageous continuous process conduction. Preferably an autoclave is used which, for thorough mixing of the reaction partners, has a suitable agitator means in order especially to shorten the reaction times.

It has been shown above that for implementing the process of the invention for silylizing carbohydrates it is preferred to assure exclusion of moisture, especially in the case of low-molecular carbohydrates. This is true also for the handling of the various reaction products because of their great sensitivity to hydrolysis. Thus, tests were made with moisture-sensitive substances in apparatus thoroughly heated and cooled under inert gas. Argon was used as inert gas (Welding Argon 4.6), which had been purified and dried with a Normag gas purifier. Also Normag glassware was used for preparative work. The reactions in liquid ammonia (99.8%) were carried out in a special steel autoclave (material number 1.4571) holding 55 cc. Ammonia was pumped in in liquid form. All hygroscopic and water-miscible solvents were tested before use for presence of moisture by IR spectroscopy. All carbohydrates, such as cellulose (cotton linters and spruce pulp of the Fluka Company), various starches and dextrins (Cerestar, Roquette) as well as sucrose, were dried to constant weight in oil pump vacuum at 70° C. All other chemicals, unless otherwise stated in the test description of the following examples, were used without further purification. The process of the invention can be carried out successfully also if some small amount of moisture is present, as small amounts of water are readily used up by a siltlizing agent present in excess.

The process of the invention avoids the corrosion problems connected with the known processes in conjunction with chlorotrimethyl silane. Moreover, no degradation takes place in the silylization. Therefore, the degree of polymerization remains constant.

The products obtained by the process of the invention are chemically and structurally comparable to the initially described known products with regard to their chemical properties. They have, however, different special features, as in particular insolubility in polar solvents. In particular they are largely free from impurities, which is not true of the known process products.

The purity is due to the fact that fewer substances are required for their production and that the compound group of formula (II), in particular in the form of ammonia, can be evaporated without a problem. The purity offers advantages in subsequent processing, as for example in the current production of regenerated cellulose fibers. The regenerated cellulose fibers can be obtained by melt-spinning as well as wet spinning. In melt-spinning, the silylized cellulose is melted and spun to a thin thread. Then this thin thread is desilylized in an acid medium. In wet spinning, the silylized cellulose is dissolved in a suitable solvent, in particular in the form of hexane, toluene and tetrahydrofurane, the jet of solution being passed into an acid precipitation bath, in particular in the form of a mixture of isopropanol, water and HCl, or methanol, water and HCl. As stated in the introduction, these measures are state of the art. However, it has been found that the regenerated cellulose fibers obtained in this manner from the silylized starting materials according to the invention show favorable tensile strength values. The xanthogenate process referred to is objectionable because it heavily pollutes the environment. The effluents contain sodium sulfate, zinc sulfate, sulfuric acid and major amounts of carbon disulfide and hydrogen sulfide, which must be removed before discharge into the drainage system, at great engineering and financial cost.

Another advantage of the process of the invention is that ammonia, if used, can easily be evaporated by lowering the pressure or opening the autoclave and also can later readily be used for another purpose. The same is true of the silylizing agents used, in particular hexamethyl disilazane, which can be recovered from the resulting hexamethyl disiloxane by known methods. Concerning this, reference is made to Journal of Applied Polymer Science vol. 26, 3832 (1981), John Wiley & Sons, Inc. Lastly, according to the invention a higher degree of silylization can be reached, in particular of more than 2.5 and, if desired, up to 3. The following examples and comparison examples will show this. To be able to make an objective relevant comparison, always the same cellulose starting materials were used. A higher degree of substitution leads to better thermal stability. Higher heating is thus possible, resulting in a favorable viscosity when spinning the melt.

The present invention will be elucidated still more specifically with reference to the following examples.

EXAMPLE 1

(Production of octuplo-(trimethylsilyl) sucrose)

In a baked-out autoclave with magnetic agitator, 3.61 g (10.55 mmole) sucrose are mixed with 0.077 ml (50.61 mmole) hexamethyldisilazane under exclusion of moisture. After pumping in 27.5 g ammonia, the autoclave is thermostated to 50° C. and the reaction mixture is stirred for 14 hours. Because of the great hydrolysis sensitivity of the reaction product, exclusion of moisture must be strictly observed during all operations. After cooling to room temperature, the ammonia is slowly evaporated by cautious opening of the inlet valve. The ammonia having evaporated, the viscous brown crude product is disolved in 100 ml n-hexane. The product is decanted from solid impurities and the n-hexane is removed by distillation at normal pressure. The residual yellow oil is subjected to high-vacuum distillation in a bulb tube still. The yield of product was 7.7 g (79% of the theory). The properties of the product can be described as follows:

B.P.$_{0.05}$: 200° C. (according to J. Org. Chem. 23, 773 (1958)): 190°–200° C. $n^{20}{}_D$: 1.4440 (acc, to J. Org. Chem. 23, 773 (1958) and Makromol. Chem. 24, 1 (1957): 1.4434).

IR$_{(film)}$: 1256 and 750 cm$^{-1}$ (Si—CH$_3$).

$^1$H-NMR: 0.19–0.18 (6s, 72H, 3.25–3.96 (m, 12H).

(CDCl$_3$): 4.28 (d, 1H), 5.21 ppm (d, 1H).

EXAMPLE 2

(Silylization of polysaccharides)

Weighed quantities of various polysaccharides, hexamethyl disilazane and ammonia were placed in the autoclave and reacted under different reaction conditions according to the following Table I. The reeaction took place as indicated in the above Example 1 under the conditions mentioned in Table I. Let cool to room temperature and slowly evaporate the ammonia by carefully opening the inlet valve. Then the reaction product remaining in the autoclave is freed of volatile components in oil pump vacuum at 60° C. This crude product is dissolved in nonpolar solvents, such as n-hexane, cyclohexane or toluene. Extremely viscous solutions are thereby formed, which at concentrations higher than 0.5% by weight contain finely divided, merely swelled gel fractions which deposit on the bottom of the vessel overnight. At room temperature these solutions gel from about 5% by weight on. After precipitation with ethanol, the white solid substance is suctioned off, washed with ethanol, and dried in oil pump vacuum at 70° C.

TABLE 1

Silylization of polysaccharides with HMDS in liquid ammonia

| No. | Polysaccharide: Type, pretreatment DP$^{a)}$ | Si(CH$_3$)$_3$/ OH$^{b)}$ | $^m$HMDS (g) | $^m$poly-saccharide (g) | $^m$NH$_3$ (g) | T (°C.) | t (h) | Yield (%) | Elementary analysis$^{c)}$ (C$_{15}$H$_{34}$O$_5$Si$_3$)$_n$ calc. C: 47.58 | H: 9.05 | DS$^{d)}$ | I$_{rel}$$^{e)}$ |
|---|---|---|---|---|---|---|---|---|---|---|---|---|
| 1 | Linters (Fluka, DP 1100) | 1:1 | 7.45 | 5 | 18 | 90 | 4 | 80 | C: 47.3 | H: 8.8 | 2.5 | 0.182 |
| 2 | Linters (Fluka, DP 1100) | 25:1 | 36 | 1 | 18 | 90 | 4 | 82 | C: 47.3 | H: 8.9 | 2.5 | 0.182 |
| 3 | Linters reprecipitated from cuoxam | 13:1 | 19 | 1 | 10 | 100 | 50 | 79 | C: 47.3 | H: 9.0 | 2.8 | 0.070 |
| 4 | Cellulose DP 290 | 13:1 | 19 | 1 | 16 | 100 | 50 | 78 | C: 47.5 | H: 8.9 | 2.9 | 0.017 |

TABLE 1-continued

Silylization of polysaccharides with HMDS in liquid ammonia

| No. | Polysaccharide: Type, pretreatment DP[a] | Si(CH$_3$)$_3$/ OH[b] | $^m$HMDS (g) | $^m$poly-saccharide (g) | $^m$NH$_3$ (g) | T (°C.) | t (h) | Yield (%) | Elementary analysis[c] (C$_{15}$H$_{34}$O$_5$Si$_3$)$_n$ calc. C: 47.58 | H: 9.05 | DS[d] | I$_{rel}$[e] |
|---|---|---|---|---|---|---|---|---|---|---|---|---|
| 5 | Corn starch acid-degraded with cat. | 13:1 | 19 | 1 | 10 | 90 | 50 | 85 | C: 47.7 | H: 8.9 | 3.0 | 0.002 |
| 6 | Corn starch | 5:1 | 23 | 3 | 7 | 90 | 48 | 83 | C: 47.7 | H: 8.9 | 3.0 | 0.002 |
| 7 | Corn starch | 2.5:1 | 11.5 | 3 | 6 | 80 | 45 | 83 | C: 47.7 | H: 8.9 | 3.0 | 0.002 |
| 8 | Maltodextrin (Potato starch) | 7:1 | 23 | 2 | 13 | 100 | 50 | 78 | C: 47.5 | H: 8.9 | 2.9 | 0.006 |
| 9 | Starch acid degraded | 6:1 | 23 | 2.5 | 6 | 80 | 40 | 72 | C: 47.4 | H: 8.6 | 2.1 | 0.213 |
| 10 | Potato starch | 6:1 | 23 | 2.5 | 10 | 80 | 70 | 74 | C: 47.0 | H: 8.4 | 1.9 | 0.209 |
| 11 | Growth corn starch | 7:1 | 23 | 2 | 7 | 80 | 24 | 74 | C: 47.0 | H: 8.5 | 1.9 | 0.215 |
| 12 | Amylose (from potato starch) | 13:1 | 15.3 | 0.8 | 18 | 100 | 48 | 75 | C: 47.59 | H: 9.0 | 3.0 | 0.002 |

[a] Average degree of polymerization, determined viscosimetrically with cellulose trinitrate
[b] Ratio of silyl groups (from HMDS used) to OH groups of the anhydroglucose units
[c] Values Calculated in % are taken as complete silylization
[d] Degree of substitution calculated from the C—H values of the elementary analyses
[e] Relative intensity of the OH valence vibration bands (IR) at 3492 cm$^{-1}$ referred to unsubstituted cellulose (I$_{rel}$cellulose = 1)

COMPARISON EXAMPLE 1

(Silylization of cellulose (cotton linters)/Comparison with Example 2)
Method a (described inter alia in J. Am. Chem. Soc. 70, 1919 (1948))

In a 250 ml two-neck inert gas flask baked out under argon, with magnetic agitator, dropping funnel, reflux condenser and calcium chloride drying tube, 2 g (12.3 mmole) cellulose are suspended in 60 ml dry pyridine and heated with reflux for 1 hour. Cool to room temperature and within 30 min add drop by drop 8 g (73.6 mmole) chlorotrimethyl silane, dissolved in 50 ml n-hexane. After stirring for 8 hours at room temperature one obtains a slightly cloudy viscous solution, which is poured into 300 ml methanol. The white fibrous solid thus obtained is suctioned off, washed twice with 100 ml methanol each time and dried for 6 hours in oil pump vacuum (0.06 mbar) at 65° C. For further purification the product is precipitated from n-hexane in ethanol and dried again. The yield is 3.96 g (85% of the theory). The properties of the product were as follows:

IR(film): 3492 cm$^{-1}$ (O—H), 1255, 840 and 755 cm$^{-1}$ (Si—CH$_3$).
Elementary analysis: calc. C: 47.58 H: 9.05 (C$_{15}$H$_{34}$O$_5$Si$_3$)$_n$ M=378.65 g/mole found C: 47.2 H: 8.4.
Degree of substitution: 2.3.

Method b (desribed inter alia in Carbohyd. Res. 31, 407 ff (1973))

In a 500 ml one-neck inert gas flask baked out under argon, with magnetic agitator, applied dropping funnel, bubble counter and calcium chloride drying tube, 5 g (30.8 mmole) cellulose are stirred in 150 ml dry formamide for 6 hours at 80° C. The solution is cooled to room temperature and slowly mixed with 100 ml (0.47 mole) hexamethyl disilazane while stirring. After completed addition, the temperature is raised to 70° C. for 2 hours. The viscous mixture is cooled to room temperature and poured into 500 ml anhydrous acetone under inteensive agitation. The precipitating white product is filtered off, washed several times with acetone, and dried in oil pump vacuum for 3 hours at 50° C. The yield was 10.19 g (87% of the theory). The properties were as follows:

IR$_{(film)}$: 3492 cm$^{-1}$ (O—H), 1255, 840 and 755 cm$^{-1}$ (Si—CH$_3$).
Elementary analysis: calc. C: 47.58 H: 9.05 (C$_{15}$H$_{34}$O$_5$Si$_3$)$_n$ M=378.65 g/mole found C: 46.9 H: 8.2.
Degree of substitution: 1.9.

Method c (described in Polym. Sci. Part A-17, 1947 ff (1969))

In a 500-ml two-neck inert gas flask baked out under argon, with magnetic agitator, dropping funnel, reflux condenser and calcium chloride drying tube, 1.2 g (7.4 mmole) cellulose in a mixture of 100 ml dry pyridine and 100 ml dry dimethyl formamide are reacted with 10 ml (59 mmole) N,O-bis (trimethylsilyl) acetamide at an oil bath temperature of 150°–160° C. After 1 hour, 150 ml toluene are added and the mixture is stirred for another 4 hours at 150° C. The cloudy mixture is cooled to room temperature and introduced into 1.5 ltr methanol under intensive agitation. The precipitating white fibers are washed with methanol and dried in oil pump vacuum at 50° C. The yield was 1.61 g (70% of the theory). The properties are as follows:

IR(film): 3492 cm$^{-1}$ (O—H), 1255, 840 and 755 cm$^{-1}$ (Si—CH$_3$).
Elementary analysis: calc. C: 47.58 H: 9.05 (C$_{15}$H$_{34}$O$_5$Si$_3$)$_n$ M=378.65 g/mole found C: 47.0 H: 8.5.
Degree of substitution: 2.0.

Method d (described in "Das Papier" 38, 607 ff (1984))

In a 100-ml one-neck flask, 1 g cellulose is suspended in 50 ml water and stored in the refrigerator overnight. The cellulose is suctioned off sharply, suspended in 50 ml dimethyl acetamide, and after 30 min again isolated by filtration. The product is resuspended in 50 ml dimethyl acetamide, letting the suspension stand overnight in the refrigerator. The cellulose thus activated is filtered off and used wet with solvent.

In a 250-ml two-neck inert gas flask baked out under argon, with magnetic agitator, dropping funnel, reflux condenser and calcium chloride drying tube, 1 g (6.2 mmole) of the activated cellulose is dissolved in a solution of 5 g lithium chloride in 100 ml dry dimethyl acetamide. The solution is heated to 80° C. while stirring and mixed with 10 ml (47 mmole) hexamethyl disilazane at this temperature within 1 hour. The occur-ring colorless precipitate is suctioned off after the reaction mixture has cooled to room temperature, washed several times with methanol, and dried in oil pump vacuum at 50° C.

The yield is 1.61 g (70% of the theory). The properties of the product are as follows:

IR$_{(film)}$: 3492 cm$^{-1}$ (O—H), 1255, 840 and 755 cm$^{-1}$ (Si—CH$_3$).

Elementary analysis: calc. C: 47.58 H: 9.05 (C$_{15}$H$_{34}$O$_5$Si$_3$)$_n$ M=378.65 g/mole found C: 46.9 H: 8.5.

Degree of substitution: 2.0.

We claim:

1. A process for the silylization of a carbohydrate which consists of reacting said carbohydrate at a temperature of 25° to 150° C. with a silylization agent having formula (I)

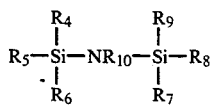

in a liquid nitrogen compound having the formula (II)

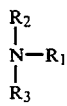

under such a pressure that a sufficient part of said nitrogen compound of formula II is in the liquid state, each of said R$_1$, R$_2$, R$_3$, R$_4$, R$_5$, R$_6$, R$_7$, R$_9$, R$_9$, R$_{10}$ being independently of each other, a member selected from the group consisting of hydrogen, a lower alkyl group of 1 to 4 carbon atoms, a cycloalkyl of 3 to 6 carbon atoms, phenyl, naphthyl, aralkyl of 7 to 18 carbon atoms, alkylaryl of 7 to 18 carbon atoms and O-, S-, or N-heterocyclic ring of 2 to 5 carbon atoms.

2. The process according to claim 1, wherein said reaction is carried out at a temperature in the range of 50° to 120° C.

3. The process according to claim 1, wherein said reaction is carried out under conditions of exclusion of moisture.

4. The process according to claim 1 wherein in said compound of formula (II) each of R$_1$, R$_2$ and R$_3$ is a member selected from the group consisting of methyl and hydrogen.

5. The process according to claim 1 wherein said silylization agent is hexamethyl disilazane.

6. The process according to claim 1 wherein said carbohydrate and said silylization agent are reacted in an inert solvent which is liquid at ambient temperatures of approximately 20° C.

7. The process according to claim 1 wherein said carbohydrate is sucrose, starch or cellulose.

8. The process according to claim 3, wherein said exclusion of moisture is achieved by drying said carbohydrate, said silylization agent, said liquid nitrogen compound and said inert solvent.

9. The process according to claim 4 wherein said nitrogen compound of formula (II) is ammonia.

10. The process according to claim 6 wherein said solvent is hexane, toluene or a mixture thereof.

11. The process of preparing a silylized acylated cellulose which consists of reacting a silylized cellulose prepared by reacting cellulose at a temperature of 25° to 150° C. with a silylization agent having formula (I)

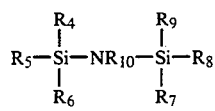

in a liquid nitrogen compound having the formula (II)

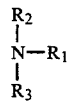

under such a pressure that a sufficient part of said nitrogen compound of formula II is in the liquid state, each of said R$_1$, R$_2$, R$_3$, R$_4$, R$_5$, R$_6$, R$_7$, R$_8$, R$_9$, R$_{10}$ being independently of each other, a member selected from the group consisting of hydrogen, lower alkyl of 1 to 4 carbon atoms, a cycloalkyl of 3 to 6 carbon atoms, phenyl, naphthyl, aralkyl of 7 to 18 carbon atoms, alkylaryl of 7 to 18 carbon atoms and O-, S-, or N-heterocyclic ring of 2 to 5 carbon atoms, wherein residual hydroxyl groups are present, with an acylating agent and isolating said silylized acylated cellulose from the reaction mixture.

12. The process according to claim 11 wherein said acylating agent is acetic anhydride or acetyl chloride.

13. The method of regenerating cellulose fibers which consists of melt spinning a silylized cellulose prepared by reacting cellulose at a temperature of 25° to 150° C. with a silylization agent having formula (I)

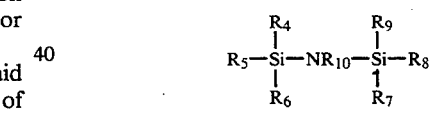

in a liquid nitrogen compound having the formula (II)

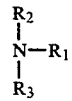

under such a pressure that a sufficient part of said nitrogen compound of formula II is in the liquid state, each of said R$_1$, R$_2$, R$_3$, R$_4$, R$_5$, R$_6$, R$_7$, R$_8$, R$_9$, R$_{10}$ being independently of each other, a member selected from the group consisting of hydrogen, lower alkyl of 1 to 4 carbon atoms, a cycloalkyl of 3 to 6 carbon atoms, phenyl, naphthyl, aralkyl of 7 to 18 carbon atoms, alkylaryl of 7 to 18 carbon atoms and O-, S-, or N-heterocyclic ring of 2 to 5 carbon atoms, to obtain spun silylized cellulose, and reacting said spun silylized cellulose with an acid whereby regenerated cellulose fibers are obtained.

14. The method of regenerating cellulose fibers which consists of wet spinning a silylized cellulose prepared by reacting cellulose at a temperature of 25° to 150° C. with a silylization agent having formula (I)

in a liquid nitrogen compound having the formula (II)

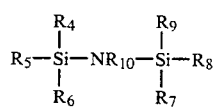

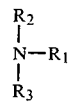

under such a pressure that a sufficient part of said nitrogen compound of formula II is in the liquid state, each of said $R_1$, $R_2$, $R_3$, $R_4$, $R_5$, $R_6$, $R_7$, $R_8$, $R_9$, $R_{10}$ being independently of each other, a member selected from the group consisting of hydrogen, a lower alkyl of 1 to 4 carbon atoms, a cycloalkyl of 3 to 6 carbon atoms, phenyl, naphthyl, aralkyl of 7 to 18 carbon atoms, alkylaryl of 7 to 18 carbon atoms and O-, S-, or N-heterocyclic ring of 2 to 5 carbon atoms, to obtain spun silylized cellulose, and reacting said spun silylized cellulose with an acid whereby regenerated cellulose fibers are obtained.

* * * * *